US006763559B2

United States Patent
Edens

(10) Patent No.: US 6,763,559 B2
(45) Date of Patent: Jul. 20, 2004

(54) COLD DRAWING PROCESS OF POLYMERIC YARNS SUITABLE FOR USE IN IMPLANTABLE MEDICAL DEVICES

(75) Inventor: Wesley I. Edens, Wayne, NJ (US)

(73) Assignee: SciMed Life Systems, Inc., Maple Grove, MN (US)

( * ) Notice: Subject to any disclaimer, the term of this patent is extended or adjusted under 35 U.S.C. 154(b) by 145 days.

(21) Appl. No.: 10/132,526

(22) Filed: Apr. 25, 2002

(65) Prior Publication Data

US 2003/0200637 A1 Oct. 30, 2003

(51) Int. Cl.⁷ .............................. D02J 1/22; D02J 13/00
(52) U.S. Cl. ...................... 28/245; 28/220; 264/210.8
(58) Field of Search ................... 28/245, 246, 240, 28/244, 172.2, 220, 258; 264/288.4, 290.5, 290.7, 291, 103, 210.8, 211.12, 210.7, 210.2, 210.3, 289.3; 57/310, 315, 362

(56) References Cited

U.S. PATENT DOCUMENTS

| | | | |
|---|---|---|---|
| 3,966,867 A | 6/1976 | Munting | |
| 4,001,367 A | * 1/1977 | Guthrie et al. | 264/154 |
| 4,003,974 A | 1/1977 | Chantry et al. | |
| 4,064,214 A | 12/1977 | FitzGerald | |
| 4,290,987 A | * 9/1981 | Soehngen et al. | 264/41 |
| 4,414,169 A | * 11/1983 | McClary | 264/210.7 |
| 4,461,740 A | * 7/1984 | Koschinek et al. | 28/245 |
| 4,482,516 A | 11/1984 | Bowman et al. | |
| 4,491,657 A | 1/1985 | Saito et al. | |
| 4,869,958 A | 9/1989 | Murase et al. | |
| 4,950,539 A | * 8/1990 | Specker et al. | 264/210.8 |
| 4,970,038 A | * 11/1990 | Stanko | 264/130 |
| 5,070,185 A | * 12/1991 | Stanko | 264/210.8 |
| 5,098,625 A | 3/1992 | Huang et al. | |
| 5,238,740 A | 8/1993 | Simons et al. | |
| 5,286,324 A | 2/1994 | Kawai et al. | |
| 5,340,517 A | 8/1994 | Koschinek et al. | |
| 5,387,300 A | 2/1995 | Kitamura | |
| 5,562,987 A | 10/1996 | Shimizu | |
| 5,607,478 A | 3/1997 | Lentz et al. | |
| 5,686,033 A | 11/1997 | Shimizu | |
| 5,718,159 A | 2/1998 | Thompson | |
| 5,741,332 A | 4/1998 | Schmitt | |
| 5,758,562 A | 6/1998 | Thompson | |
| RE35,972 E | 11/1998 | Cuculo et al. | |
| 6,015,616 A | 1/2000 | Simons et al. | |
| 6,068,805 A | 5/2000 | Lockridge et al. | |
| 6,071,452 A | 6/2000 | Kelmartin, Jr. et al. | |
| 6,074,084 A | 6/2000 | Kolossow | |

FOREIGN PATENT DOCUMENTS

| | | |
|---|---|---|
| EP | 0451729 | 10/1991 |
| EP | 0557894 | 9/1993 |
| GB | 1592936 | 7/1981 |
| JP | 08325838 | 12/1996 |

* cited by examiner

Primary Examiner—A. Vanatta
(74) Attorney, Agent, or Firm—Hoffmann & Baron, LLP

(57) ABSTRACT

The present invention provides for a method of cold drawing polymeric yarns suitable for use in implantable medical devices, such as vascular grafts. The method of the present invention produces cold drawn polymeric yarns that have a substantially uniform linear density and a highly oriented molecular structure as well as good lubricity, non-thrombogenicity and biocompatibility. In one embodiment of the present invention there is provided a method of cold drawing multi-filament PTFE yarns include the steps of maintaining the PTFE yarn at a temperature below the glass transition temperature of the yarn, drawing the yarn at such temperature over a first roller rotated about its axis at a first speed and a second roller rotated about its axis at a speed faster than the speed of the first roller to a selected denier and to increase molecular orientation; and twisting the drawn yarn.

16 Claims, 1 Drawing Sheet

COLD DRAWING PROCESS OF POLYMERIC YARNS SUITABLE FOR USE IN IMPLANTABLE MEDICAL DEVICES

FIELD OF THE INVENTION

The present invention relates to a method of drawing polymeric yarns and more particularly, to a cold drawing process that produces polytetrafluoroethylene (PTFE) yarns suitable for use in medical devices.

BACKGROUND OF RELATED TECHNOLOGY

PTFE is used in numerous demanding applications due to its excellent physical properties, which include excellent high and low temperature performance, chemical resistance and lubricious properties. PTFE is particularly useful in medical devices such as vascular prostheses. Use of PTFE yarns for textile vascular prostheses has been limited because finished PTFE yarns suitable for use in medical devices are often not commercially available to medical device manufacturers. Unfinished PTFE yarns that are available, however, typically do not possess the physical characteristics, such as sufficient orientation, i.e. molecular alignment of the fibers, and the requisite uniform linear density necessary for such medical device uses. Unfinished PTFE yarns also typically have poor molecular orientation and uneven linear densities within the same strand of yarn. This creates problems when processing such yarns into a textile prosthesis. For instance, unfinished yarns may accumulate in the machine during the textile prosthesis manufacturing process or stretch to create a non-uniform prosthesis. Additionally, problems may occur when such prostheses made with unfinished yarns therein are placed in a body lumen because such yarns may unexpectedly and undesirably stretch. Thus, the prostheses will not perform in a consistent and predictable manner. As such, these yarns are not suitable for use in medical devices without further processing.

Conventional means to finish PTFE yarns typically involve a heat drawing process. Heat drawing results in yarns with good orientation and uniform linear density which when incorporated into a textile vascular prosthesis exhibit predictable and consistent behavior, both in the textile manufacturing process and in vivo. However, heat drawing yarns requires a heat drawing apparatus that can maintain the yarn at an elevated temperature. Thus, heat drawing is less than satisfactory since it may be expensive and difficult to control and maintain the elevated temperatures.

Accordingly, it is desirable to provide a convenient and inexpensive method for producing PTFE yarns suitable for use in medical devices that have a uniform linear density and a highly oriented molecular structure.

SUMMARY OF THE INVENTION

The present invention provides for a method of cold drawing PTFE yarn. The cold drawing method of the present invention can be performed at room temperature and does not require the use of a heat drawing apparatus. Thus, the present invention overcomes some of the disadvantages of conventional PTFE drawing techniques by providing an inexpensive and convenient method of producing PTFE yarns suitable for use in implantable medical devices, such as vascular grafts.

The method of the present invention produces cold drawn PTFE yarns that have a substantially uniform linear density and good molecular orientation as well as good lubricity, non-thrombogenicity and biocompatibility. Yarns made by the method of the present invention behave in a consistent and predictable manner thereby minimizing the in vivo problems associated with textile prosthesis manufacturing having unfinished yarns therein. Additionally, the yarns produced by the inventive methods reduce the problems associated with textile manufacturing and can be processed into textile vascular prostheses, such as woven, knitted or braided prostheses.

In one embodiment of the present invention, there is provided a method of cold drawing polymeric yarns suitable for use in implantable medical devices including the steps of maintaining the polymeric yarn at a temperature below the glass transition temperature of the yarn, drawing the yarn at such temperature over a first roller rotated about its axis at a first speed and a second roller rotated about its axis at a speed faster than the speed of the first roller, to a selected denier and to increase molecular orientation; and twisting the drawn yarn to form a yarn with a substantially uniform linear density.

In another embodiment of the present invention, there is provided a method of cold drawing multi-filament PTFE yarns suitable for use in implantable medical devices including the steps of maintaining the PTFE yarn at a temperature below the glass transition temperature of the yarn, drawing the yarn at such temperature over a first roller rotated about its axis at a first speed and a second roller rotated about its axis at a speed faster than the speed of the first roller, to a selected denier and to increase molecular orientation; and twisting the drawn yarn to form a yarn with a substantially uniform linear density.

One aspect of the present invention provides for twisting the multi-filament yarn, which encourages the multiple filaments to behave as a coherent unit. Twisting the filaments binds the filaments together and increases the tensile strength of the yarn. Additionally, twisting the yarns helps minimize filament separation and yarn static processing problems.

The present invention also contemplates providing for PTFE yarn produced by the inventive methods.

DETAILED DESCRIPTION OF THE INVENTION

Figure 1:
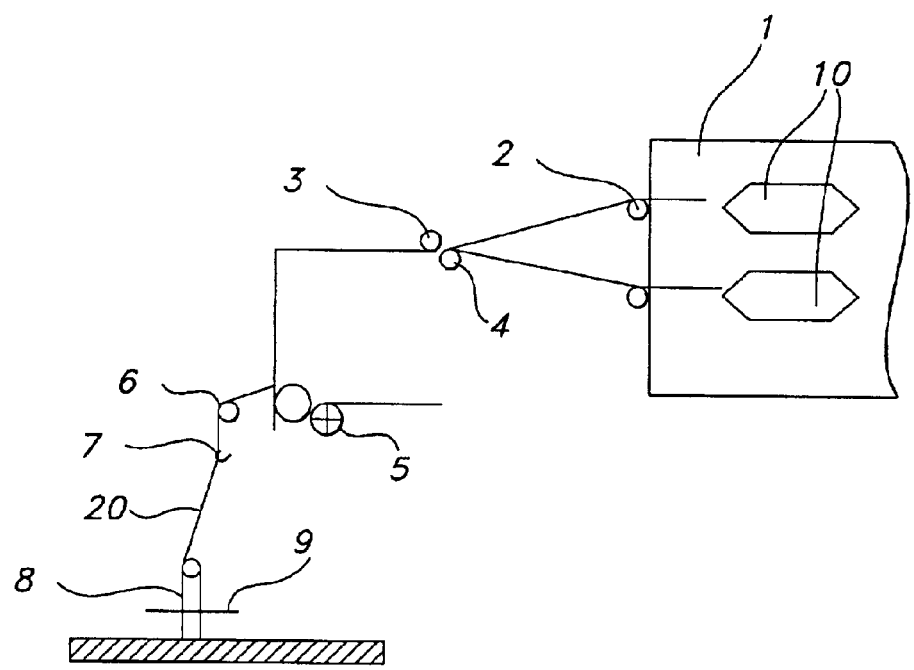
FIG. 1 shows a schematic view of the cold drawing apparatus employed as the present invention.

FIG. 1 is a schematic view of the apparatus used for the inventive cold drawing method in accordance with a preferred arrangement of the present invention. As illustrated in FIG. 1, the cold drawing method of the present invention use an apparatus that is equipped with a package creel 1 which holds the unfinished, undrawn yarn. The methods of the present invention contemplates drawing multiple yarns at the same time. For instance, two or more spindles of raw yarn 10 may be present in package creel 1. The yarns from the multiple spindles, desirably, are joined at first roller 3, and drawn contemporaneously in the drawing apparatus. Alternatively, multiple ply yarns may be prepared by combining previously drawn yarns in accordance with the present invention with or without further drawing. A multiple ply yarn is desirable to impart certain properties into the drawn yarn, such as higher tensile strength.

Yarn is fed through creel roller 2 and then drawn over first roller 3 that spins about its axis at a first speed and second roller 5, which turns about its axis at a speed faster than the speed of the first roller 3 to draw the yarn to a desired denier and to increase filament orientation. Creel roller 2 is desirably freely rotatable and the speed of first roller guide 3 and second roller 5 may be adjustable.

The properties of the drawn yarn can be tailored to meet the requirements of a particular use. For instance, properties of the drawn yarn may be altered by varying the draw ratio, twisting amount and adding multiple yarns to produce a multi-ply finished yarn. The draw speed can range from about 2000 to about 6000 meters per minute. The draw ratio indicates the ratio of the speed of the second roller 5 turning about its axis compared to first roller 3 turning about its axis. Draw ratios useful in the present invention range from about 1.05 to about 1.50. Use of draw ratios higher than 1.50 generally risk breakage of the yarn. The draw ratio is selected based on the desired tension strength, orientation and linear density of the yarn. A higher draw ratio will result in a higher reduction in the linear density of the yarn.

As shown in FIG. 1, yarn 20 leaves pigtail guide 7 and is guided onto spindle 8 and twisted by ring and traveler 9. Yarn that is not twisted may fray and separate due to the electrostatic forces present on the filaments of the yarn. Desirably, yarns are twisted which increases their strength and reduces the tendency of the filaments to fray. Generally useful twisting speeds include those from about 0.5 turns per inch (tpi) to about 20 tpi and desirably from about 0.5 tpi to about 5 tpi. Most desirably, the twisting speed is about 1.5 tpi. A conventional anti-static agent may be added to PTFE yarn to minimize static charges on the yarns.

Useful yarns include biocompatible polymers such as polyethylene terephthalate (PET), PTFE, polyurethanes, biodegradable polymers such as poly(glycolic acid) (PGA), poly(lactic acid)(PLA), polydioxanones, polyoxalates, poly(α-esters), polyanhydrides, polyacetates, polycaprolactones, poly(orthoesters), and combinations and copolymers thereof. Although PTFE yarns with multiple filaments are particularly desirable in the present invention, monofilament PTFE yarns may also be employed. Polymeric yarn, such as PTFE yarn, of any denier, uniformity and orientation are useful with the present invention. Useful unfinished, undrawn yarns may have linear densities from about 50 to about 350 denier. Yarns drawn by the inventive methods of the present invention have a highly oriented molecular structure and a substantially uniform linear density, making them particularly suitable for use in medical devices.

Desirably, the single ply drawn yarns have a linear density from about 100 to about 295 denier, depending on the application of the yarn in the medical device. Even more desirable are drawn yarns having a linear density from about 216 to about 262 denier. In one particularly desirable aspect of the invention, the yarn has about 30 filaments.

The present invention desirably maintains the temperature below the glass transition temperature (Tg) of the yarn. If the material has multiple Tg's, desirably the temperature is maintained below the maximum Tg. A suitable temperature range is from about −178° C. to about +70° C. Desirably, the temperature is maintained at room temperature, provided that room temperature is below Tg of the yarn.

Various embodiments of the present invention, are set forth in the following examples. These examples are presented for purposes of illustration only and are not intended to limit the scope of the invention.

EXAMPLES

TABLE 1

Analysis of Cold Drawn PTFE Yarn (1-ply; 5 tpi)

| Cone | | Linear Density (Denier) | Tensile Strength (g) | % Elongation | Tenacity (gm/den) |
|---|---|---|---|---|---|
| 1 | Avg. | 295.59 | 125.93 | 109.40 | 0.43 |
| | Std. Dev. | 0.82 | 5.62 | 10.92 | 0.02 |
| | Std. Dev. (%) | 0.28 | 4.46 | 9.99 | 4.99 |
| | Min. | 294.84 | 121.95 | 101.67 | 0.41 |
| | Max. | 296.46 | 129.90 | 117.12 | 0.44 |
| 2 | Avg. | 261.12 | 98.99 | 112.71 | 0.38 |
| | Std. Dev. | 0.46 | 6.64 | 4.15 | 0.03 |
| | Std. Dev. (%) | 0.18 | 6.71 | 3.68 | 7.44 |
| | Min. | 260.73 | 94.29 | 109.77 | 0.36 |
| | Max. | 261.63 | 103.68 | 115.64 | 0.40 |
| 3 | Avg. | 255.66 | 114.07 | 142.69 | 0.45 |
| | Std. Dev. | 1.99 | 2.98 | 18.38 | 0.01 |
| | Std. Dev. (%) | 0.78 | 2.61 | 12.88 | 1.59 |
| | Min. | 254.25 | 111.96 | 129.69 | 0.44 |
| | Max. | 257.94 | 116.17 | 155.68 | 0.45 |
| 4 | Avg. | 248.88 | 110.91 | 103.75 | 0.45 |
| | Std. Dev. | 0.50 | 2.60 | 2.96 | 0.01 |
| | Std. Dev. (%) | 0.20 | 2.35 | 2.86 | 1.59 |
| | Min. | 248.31 | 109.07 | 101.65 | 0.44 |
| | Max. | 249.21 | 112.75 | 105.84 | 0.45 |
| 5 | Avg. | 255.78 | 96.95 | 105.53 | 0.38 |
| | Std. Dev. | 0.95 | 4.79 | 0.98 | 0.01 |
| | Std. Dev. (%) | 0.37 | 4.94 | 0.93 | 3.72 |
| | Min. | 255.06 | 93.56 | 104.83 | 0.37 |
| | Max. | 256.86 | 100.33 | 106.22 | 0.39 |
| 6 | Avg. | 291.39 | 127.08 | 124.22 | 0.44 |
| | Std. Dev. | 0.45 | 0.28 | 0.22 | 0.00 |
| | Std. Dev. (%) | 0.16 | 0.22 | 0.18 | 0.00 |
| | Min. | 290.97 | 126.88 | 124.06 | 0.44 |
| | Max. | 291.87 | 127.27 | 124.37 | 0.44 |

Table 1 displays the results of tests evaluating the physical properties of several cold drawn PTFE yarn samples classified by the manufacturer as having linear density of about 225 denier with 30 filaments. The yarn samples were drawn at room temperature using the methods of the present invention. Each sample was tested in three different spots along the yarn. The average linear density of the yarns ranged on average from about 254 to about 296 denier. The standard deviation of each individual drawn lot was good in a commercially acceptable range for implants, i.e., ranging from about 0.5 to about 2.0 denier; from about 0.2% to about 0.8%. Tensile strength of the yarn was measured on an Instron Tensile Tester. The yarns tested also had excellent tensile strength, ranging on average from about 94 grams to about 129 grams. The percent elongation values were also calculated from measurements on an Instron. The percent elongation of the samples were also excellent, ranging on average from about 101 to about 156. The tenacity of the drawn yarn was also found to be good for commercial use in implants and ranged from about 0.36 to about 0.45 grams/denier. Refer to Table 1, page 8.

The drawn yarns in Table 1 were used to form a single-ply (5 TPI) yarn using the drawing and twisting apparatus of the present invention. The same pretension was applied to the first roller and the second roller so that the two-ply yarn was not further drawn. Cone sample A in Table 2, page 11, is a combination of cone 1 and 6 from Table 1, page 8. Cone sample B in Table 2 is a combination of cone 5 and 3 from Table 1. Cone sample C in Table 2, page 11, is a combination of cone 4 and 2 from Table 1, page 8.

As is shown by Table 2, favorable results were obtained by combining two individually cold drawn PTFE yarns to make a two-ply yarn. The properties of the resulting two-ply yarns are displayed in Table 2. The linear density of the two-ply yarns ranged from about 495 to about 567 denier. The tensile strength ranged on average from about 158 to about 244 grams. The percent elongation and tenacity values remained roughly similar to the values of the individually drawn yarns. The percent elongation ranged on average from about 77 to about 114 and the tenacity ranged from about 0.32 to about 0.41 grams per denier.

TABLE 2

Analysis of Cold Drawn PTFE Yarn (2-Ply; 5 tpi)

| Cone | | Linear Density (Denier) | Tensile Strength (g) | % Elongation | Tenacity (gm/den) |
|---|---|---|---|---|---|
| A | Trial 1 | 567.27 | 232.73 | 109.31 | 0.41 |
| | Trial 2 | 568.08 | 225.70 | 101.47 | 0.40 |
| | Trial 3 | 570.87 | 244.36 | 114.89 | 0.43 |
| | Avg. | 568.74 | 234.26 | 108.56 | 0.41 |
| | Std. Dev. | 1.89 | 9.42 | 6.74 | 0.02 |
| | Std. Dev. (%) | 0.33 | 4.02 | 6.21 | 3.70 |
| | Min. | 567.27 | 225.70 | 101.47 | 0.40 |
| | Max. | 570.87 | 244.36 | 114.89 | 0.43 |
| B | Trial 1 | 508.95 | 170.83 | 89.57 | 0.34 |
| | Trial 2 | 508.59 | 161.37 | 82.90 | 0.32 |
| | Trial 3 | 509.94 | 157.95 | 76.96 | 0.31 |
| | Avg. | 509.16 | 163.38 | 83.14 | 0.32 |
| | Std. Dev. | 0.70 | 6.67 | 6.31 | 0.02 |
| | Std. Dev. (%) | 0.14 | 4.08 | 7.59 | 4.72 |
| | Min. | 508.59 | 157.95 | 76.96 | 0.31 |
| | Max. | 509.94 | 170.83 | 89.57 | 0.34 |
| C | Trial 1 | 495.09 | 184.83 | 75.10 | 0.37 |
| | Trial 2 | 494.55 | 189.03 | 95.35 | 0.38 |
| | Trial 3 | 494.82 | 188.77 | 80.65 | 0.38 |
| | Avg. | 494.82 | 187.54 | 83.70 | 0.38 |
| | Std. Dev. | 0.27 | 2.35 | 10.46 | 0.01 |
| | Std. Dev. (%) | 0.05 | 1.25 | 12.50 | 1.53 |
| | Min. | 494.55 | 184.83 | 75.10 | 0.37 |
| | Max. | 495.09 | 189.03 | 95.35 | 0.38 |

TABLE 3

Analysis of Cold Drawn PTFE Yarn (5 tpi)

| Cone | | Linear Density (Denier) | Tensile Strength (g) | % Elongation | Tenacity (gm/den) |
|---|---|---|---|---|---|
| 1 | Trial 1 | 262.71 | 176.15 | 104.56 | 0.67 |
| | Trial 2 | 261.36 | 182.92 | 112.35 | 0.70 |
| | Trial 3 | 262.71 | 180.82 | 95.17 | 0.69 |
| | Avg. | 262.26 | 179.96 | 104.03 | 0.69 |
| | Std. Dev. | 0.78 | 3.47 | 8.60 | 0.02 |
| | Std. Dev. (%) | 0.30 | 1.93 | 8.27 | 2.22 |
| | Min. | 261.36 | 176.15 | 95.17 | 0.67 |
| | Max. | 262.71 | 182.92 | 112.35 | 0.70 |
| 2 | Trial 1 | 255.42 | 207.3 | 81.79 | 0.81 |
| | Trial 2 | 255.96 | 198.69 | 84.1 | 0.78 |
| | Trial 3 | 254.79 | 210.91 | 84.55 | 0.83 |
| | Avg. | 255.39 | 205.63 | 83.48 | 0.81 |
| | Std. Dev. | 0.59 | 6.28 | 1.48 | 0.03 |
| | Std. Dev. (%) | 0.23 | 3.05 | 1.77 | 3.12 |
| | Min. | 254.79 | 198.69 | 81.79 | 0.78 |
| | Max. | 255.96 | 210.91 | 84.55 | 0.83 |
| 3 | Trial 1 | 241.47 | 201.58 | 90.51 | 0.81 |
| | Trial 2 | 254.61 | 191.99 | 82.75 | 0.77 |
| | Trial 3 | 254.16 | 196.13 | 73.98 | 0.78 |
| | Avg. | 250.08 | 196.57 | 82.41 | 0.79 |
| | Std. Dev. | 7.46 | 4.81 | 8.27 | 0.02 |
| | Std. Dev. (%) | 2.98 | 2.45 | 10.03 | 2.65 |
| | Min. | 241.47 | 191.99 | 73.98 | 0.77 |
| | Max. | 254.61 | 201.58 | 90.51 | 0.81 |
| 4 | Trial 1 | 216.72 | 202.5 | 47.65 | 0.93 |
| | Trial 2 | 216.36 | 200.01 | 38.98 | 0.92 |
| | Trial 3 | 218.25 | 201.58 | 46.82 | 0.93 |
| | Avg. | 217.11 | 201.36 | 44.48 | 0.93 |
| | Std. Dev. | 1.00 | 1.26 | 4.78 | 0.01 |
| | Std. Dev. (%) | 0.46 | 0.63 | 10.75 | 0.62 |
| | Min. | 216.36 | 200.01 | 38.98 | 0.92 |
| | Max. | 218.25 | 202.50 | 47.65 | 0.93 |
| 5 | Trial 1 | 253.89 | 196 | 71.31 | 0.79 |
| | Trial 2 | 255.42 | 193.37 | 78.15 | 0.77 |
| | Trial 3 | 239.67 | 200.66 | 86.9 | 0.80 |
| | Avg. | 249.66 | 196.68 | 78.79 | 0.79 |
| | Std. Dev. | 8.69 | 3.69 | 7.81 | 0.02 |
| | Std. Dev. (%) | 3.48 | 1.88 | 9.92 | 1.94 |
| | Min. | 239.67 | 193.37 | 71.31 | 0.77 |
| | Max. | 255.42 | 200.66 | 86.90 | 0.80 |
| 6 | Trial 1 | 256.77 | 189.56 | 65.98 | 0.74 |
| | Trial 2 | 258.66 | 191.2 | 64.62 | 0.74 |
| | Trial 3 | 257.22 | 195.01 | 67.41 | 0.76 |
| | Avg. | 257.55 | 191.92 | 66.00 | 0.75 |
| | Std. Dev. | 0.99 | 2.80 | 1.40 | 0.01 |
| | Std. Dev. (%) | 0.38 | 1.46 | 2.11 | 1.55 |
| | Min. | 256.77 | 189.56 | 64.62 | 0.74 |
| | Max. | 258.66 | 195.01 | 67.41 | 0.76 |
| 7 | Trial 1 | 261.00 | 176.61 | 73.97 | 0.67 |
| | Trial 2 | 262.35 | 182.33 | 62.44 | 0.69 |
| | Trial 3 | 265.59 | 171.82 | 75.18 | 0.65 |
| | Avg. | 262.98 | 176.92 | 70.53 | 0.67 |
| | Std. Dev. | 2.36 | 5.26 | 7.03 | 0.02 |
| | Std. Dev. (%) | 0.90 | 2.97 | 9.97 | 2.99 |
| | Min. | 261.00 | 171.82 | 62.44 | 0.65 |
| | Max. | 265.59 | 182.33 | 75.18 | 0.69 |
| 8 | Trial 1 | 256.95 | 174.84 | 75.24 | 0.68 |
| | Trial 2 | 259.02 | 175.01 | 86.12 | 0.68 |
| | Trial 3 | 260.1 | 176.68 | 93.45 | 0.68 |
| | Avg. | 258.69 | 175.51 | 84.94 | 0.68 |
| | Std. Dev. | 1.60 | 1.02 | 9.16 | 0.00 |
| | Std. Dev. (%) | 0.62 | 0.58 | 10.79 | 0.00 |
| | Min. | 256.95 | 174.84 | 75.24 | 0.68 |
| | Max. | 260.10 | 176.68 | 93.45 | 0.68 |
| 9 | Trial 1 | 257.49 | 174.71 | 77.95 | 0.68 |
| | Trial 2 | 257.94 | 174.84 | 70.57 | 0.68 |
| | Trial 3 | 260.46 | 170.77 | 84.15 | 0.66 |
| | Avg. | 258.63 | 173.44 | 77.56 | 0.67 |
| | Std. Dev. | 1.60 | 2.31 | 6.80 | 0.01 |
| | Std. Dev. (%) | 0.62 | 1.33 | 8.77 | 1.71 |
| | Min. | 257.49 | 170.77 | 70.57 | 0.66 |
| | Max. | 260.46 | 174.84 | 84.15 | 0.68 |
| 10 | Trial 1 | 245.16 | 154.47 | 112.66 | 0.62 |
| | Trial 2 | 247.86 | 157.95 | 87.76 | 0.64 |
| | Trial 3 | 248.58 | 160.39 | 72.24 | 0.65 |
| | Avg. | 247.20 | 157.60 | 90.89 | 0.64 |
| | Std. Dev. | 1.80 | 2.98 | 20.39 | 0.02 |
| | Std. Dev. (%) | 0.73 | 1.89 | 22.44 | 2.40 |
| | Min. | 245.16 | 154.47 | 72.24 | 0.62 |
| | Max. | 248.58 | 160.39 | 112.66 | 0.65 |

Table 3 displays the results of drawing trials of a cone of PTFE yarn. The average linear density of the individual samples ranged from about 245 to about 265 denier with an average of 256.8 denier. The tensile strength of the yarns ranged on average from 154 to about 182 grams. The percent elongation values ranged on average from about 62 to about 113 and the tenacity ranged from about 0.62 to about 0.69 grams per denier.

It was determined that the cold drawing method of the present invention results in PTFE yarns with a substantially uniform linear density so that such PTFE yarns are suitable for use in implantable medical devices.

In accordance with the present invention, there is provided an implantable textile prosthesis and more specifically, an implantable textile prosthesis having cold drawn PTFE yarns with a substantially uniform linear density and a highly oriented molecular structure. The present invention contemplates implantable prostheses, such as endovascular grafts, balloon catheters, meshes, vascular patches, hernia plugs, stent-graft composites, blood filters and the like. One embodiment of the present invention contemplates a tubular implantable prosthesis. Examples of prostheses that may require a tubular design include intraluminal prostheses, endovascular grafts, and radially deformable support components, such as radially deformable stents. Examples of the prosthesis of the present invention are more particularly described in commonly owned patent application, Application Ser. No. 10/132,367, entitled "Implantable Textile Prostheses Having PTFE Cold Drawn Yarns," filed Apr. 25, 2002, and incorporated herein by reference.

The invention being thus described, it will now be evident to those skilled in the art that the same may be varied in many ways. Such variations are not to be regarded as a departure from the spirit and scope of the invention and all such modifications are intended to be included within the scope of the following claims.

What is claimed:

1. A method of cold drawing polymeric yarns suitable for use in implantable medical devices comprising:
   a. maintaining said yarn at a temperature below the glass transition temperature of said yarn;
   b. drawing said yarn at said temperature over a first roller rotated about its axis at a first speed and a second roller rotated about its axis at a speed faster than the speed of said first roller to draw the yarn to a selected denier and to increase molecular orientation; and
   c. twisting said drawn yarn to form a yarn having a substantially uniform linear density, wherein said yarn has a minimum tenacity of at least about 0.32 grams per denier and further wherein said yarn has a maximum tenacity of about 0.93 grams per denier.

2. The method of claim 1, wherein said yarn has a linear density from about 150 denier to about 295 denier.

3. The method of claim 1, wherein said second roller is rotated from about 1.05 to about 1.5 times faster than said first roller.

4. The method of claim 1, wherein said twisting ranges between about 0.5 to about 10 twists per inch.

5. The method of claim 4, wherein said twisting is 1.5 twists per inch.

6. The method of claim 1, further including the step of applying an anti-static lubricant to said yarn.

7. The method of claim 1, wherein said yarn is selected from the group consisting of polyethylene terephthalate, polytetrafluoroethylene and combinations thereof.

8. The method of claim 1, wherein said temperature is room temperature.

9. The method of claim 1, wherein said yarn comprises multiple filaments.

10. The method of claims 1, wherein said yarn comprises 30 filaments.

11. A textile prosthesis comprising polymeric yarns produced by the method of claim 1.

12. A method of cold drawing multi-filament PTFE yarns suitable for use in implantable medical devices comprising:
   a. maintaining said PTFE yarn at a temperature below the glass transition temperature of said yarn;
   b. drawing said yarn at said temperature over a first roller rotated about its axis at a first speed and a second roller rotated about its axis at a speed faster than the speed of said first roller to draw the yarn to a selected denier and to increase molecular orientation; and
   c. twisting said drawn yarn to form a yarn having a substantially uniform linear density.

13. The method according to claim 12, wherein said medical device is a vascular prosthesis.

14. The method according to claim 12, wherein said medical device is a textile vascular prosthesis.

15. The method of claim 12, wherein said yarn has a minimum tenacity of at least about 0.32 grams per denier, and further wherein said yarn has maximum tenacity of about 0.93 grams per denier.

16. A textile prosthesis comprising PTFE yarns produced by the method of claim 15.

* * * * *